United States Patent
Bell et al.

(10) Patent No.: US 9,138,503 B2
(45) Date of Patent: Sep. 22, 2015

(54) SELECTIVELY SPINNABLE AIR FRESHENER STRUCTURE

(71) Applicant: Rotuba Extruders Inc., Linden, NJ (US)

(72) Inventors: Adam Bell, Short Hills, NJ (US); Jim Blumenfeld, Lincroft, NJ (US); Robert Coopersmith, Livingston, NJ (US); James Loof, Bergenfield, NJ (US)

(73) Assignee: Rotuba Extruders Inc., Linden, NJ (US)

( * ) Notice: Subject to any disclaimer, the term of this patent is extended or adjusted under 35 U.S.C. 154(b) by 146 days.

(21) Appl. No.: 14/026,224

(22) Filed: Sep. 13, 2013

(65) Prior Publication Data

US 2015/0076246 A1   Mar. 19, 2015

(51) Int. Cl.
*A61L 9/12* (2006.01)

(52) U.S. Cl.
CPC .............. *A61L 9/122* (2013.01); *A61L 2209/11* (2013.01)

(58) Field of Classification Search
CPC .................................. A61L 9/12; A61L 9/122
USPC ......................................................... 422/124
See application file for complete search history.

(56) References Cited

U.S. PATENT DOCUMENTS

| | | |
|---|---|---|
| 2,410,832 A | 11/1946 | McLean |
| 4,927,095 A | 5/1990 | Young |
| 4,968,456 A | 11/1990 | Muderlak et al. |
| 5,800,897 A | 9/1998 | Sharma et al. |
| 5,853,672 A | 12/1998 | Lorman et al. |
| 6,102,660 A | 8/2000 | Lee |
| 6,103,201 A | 8/2000 | Green |
| 7,032,916 B2 | 4/2006 | Plana |
| 7,143,958 B1 | 12/2006 | Dorney |
| 7,741,266 B2 | 6/2010 | Bell et al. |
| 8,096,486 B2 | 1/2012 | Wang et al. |

*Primary Examiner* — Sean E Conley
(74) *Attorney, Agent, or Firm* — Leason Ellis LLP

(57) ABSTRACT

Apparatus for dissipating a fragrance or malodor eliminator utilizes an infused disc which a user can place in either a rotating or a fixed position. The two states will dissipate a scent/malodor-eliminator at different rates. The disc is mounted on a shaft that secures the disc in an air stream. The shaft defines several positions at which the disc can be placed, as well as structures to retain the disc at a selected location along the shaft. The shaft is part of a support which includes a mechanism for securing the apparatus within the air stream. Air flow causes the disc to rotate and dissipate at one rate or to pass through a stationary disc at a second, lower rate, as a function of the position of the disc on the shaft. A method of imparting a scent or malodor eliminator to air is also disclosed.

19 Claims, 3 Drawing Sheets

SELECTIVELY SPINNABLE AIR FRESHENER STRUCTURE

FIELD OF THE INVENTION

The present relates, generally, to air fresheners, and more particularly to mechanical air freshener assemblies.

BACKGROUND OF THE INVENTION

Some air fresheners are refillable, and others are disposable. For the automotive market, for instance, there are a variety of inexpensive air fresheners. One variety is made from cardboard that has been impregnated with fragrance. Typically, the cardboard is cut-out into a generally two-dimensional shape that can hang from a rear-view mirror and so on. The diffusion profile of this type of air freshener can vary over time, from overpowering when first opened to almost no scent at all. The relatively short life span of such air fresheners is due to the fact that no attempt is made to regulate dissipation of the scent. The scent continually evaporates regardless of whether the vehicle is occupied or the vehicle's owner wants to dissipate scent at a given time.

U.S. Pat. No. 6,103,201 (Green) discloses an air freshener that employs a rotor made of a scent-bearing material to disperse a fragrance in the air flowing from a vent, for example, in a vehicle. The rotor can be molded from scented plastic (e. g., low-density polyethylene impregnated with a fragrance). The rotor is rotatably mounted to a base having a clip or fastener that can be attached to the louvers covering the vent. The air flow through the vent causes the rotor to rotate and thereby disperses the scent at a higher rate than if the rotor were stationary. However, there is no mechanism to restrain rotation or suggestion in the art to combine the stationary air freshener solutions noted above which are typically made of cardboard and rotating devices such as in the '201 patent.

It is with respect to these considerations that present invention is directed.

SUMMARY OF THE INVENTION

In accordance with one aspect of the invention, an apparatus for imparting scent into an air stream or for eliminating malodors, or both, comprises a support that is positioned in an air stream. The support includes a shaft extending to a free end. This shaft provides an axis of rotation and has two portions along the axis of rotation. The apparatus has a resiliently compressible head at the free end of the stem. A scented disc can be retained on the stem by the head. The disc has a central aperture which is sized to cause the head to compress when it is urged over the head. The disc is selectively positionable along either a first portion of the shaft or a second portion of the shaft. The disc includes a plurality of air deflectors. When the disc is disposed along the first portion, it is coupled to the shaft for rotation. In contrast, when the disc is disposed along the second portion, it is fixedly coupled to the shaft.

In accordance with another aspect of the invention, a method for imparting a scent to an air stream or for eliminating malodors, or both, comprises firstly providing a support to a vent or similar structure through which an air stream flows. The support has a shaft extending from a clip to a free end which defines an axis of rotation. The shaft also has a resiliently compressible head at the free end and has two portions along the axis of rotation. A disc having a central aperture through a broad face thereof is provided which is seatable behind the head. The head retains the disc on the stem when it is positioned behind the head. The disc includes the scent that is imparted to the air stream. According to the method, the disc rotates relative to the shaft while the disc is positioned along the first portion of the shaft behind the head, and is selectively precluded from rotation relative to the shaft while the disc is positioned along the second portion of the shaft.

These and other aspects, features and advantages will be apparent from the following description and accompanying drawing figures.

BRIEF DESCRIPTION OF THE DRAWINGS

Like reference symbols in the various drawings indicate like elements.

DESCRIPTION

By way of overview and introduction, embodiments are described in which a support structure is configured to provide the user with use-options so that the rate of dissipation can be changed as between at least two rates of imparting a scent to a stream of air, or for eliminating malodors, or both. Generally, an air freshener support structure provides multiple points of contact with a spinnable, scented disc. The different contact points can vary from low-frictional contact to high-frictional contact, which, in turn, can enable the scented disc to rotate in a range from freely to not at all.

In one particular embodiment described in connection with FIGS. 1-3, an apparatus 10 includes a rotor made of a scented material which dissipates scent. As will be appreciated from the discussion below, instead of dissipating a scent, the air freshener can be configured to disseminate a malodor eliminator, or can be configured to both dissipate a scent and disseminate a malodor eliminator. For discussion purposes only, however, the embodiment is described in regard to imparting a scent to an airstream. When in motion, the rotor dissipates scent more quickly than when it is held stationary. The apparatus allows the user to select and place the rotor at a position which either allows the rotor to rotate or that holds the rotor still. In this way, embodiments of the invention provide the user control over the rate at which the scent dissipates, because rotation will more quickly diffuse the scent from the rotor. This construction can increase the useful life of the air freshener 10 by dispensing the scent quickly only when the consumer chooses that configuration. Embodiments of the invention can add play value to toys and novelties, as will be appreciated from the discussion below.

Figure 1A:
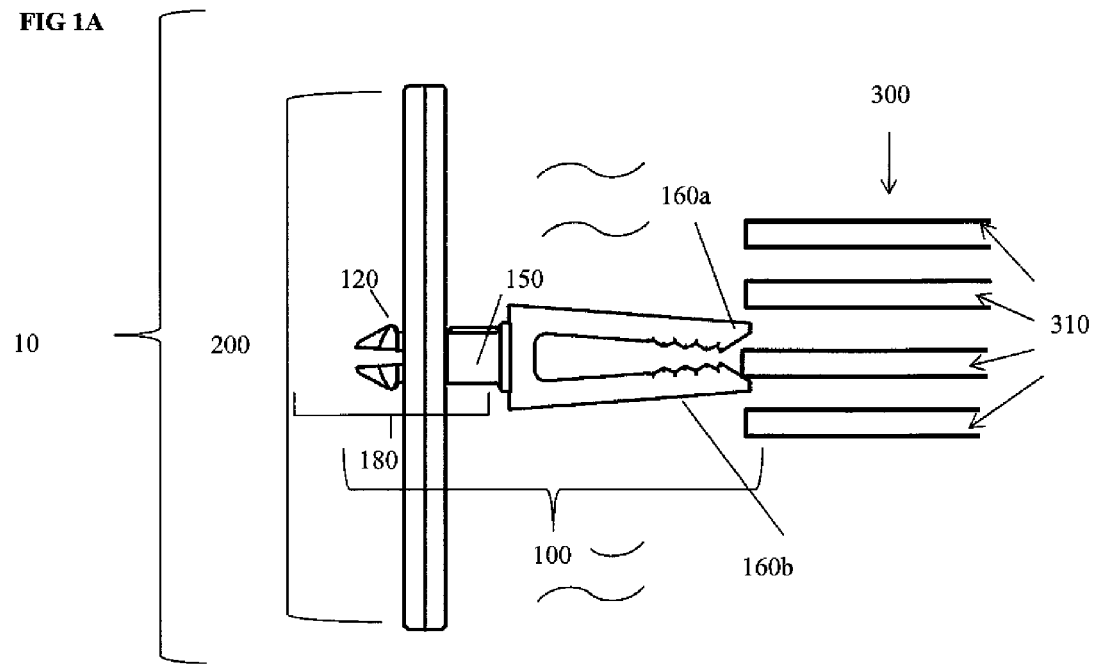
FIG. 1a is a schematic diagram that illustrates a side view of one embodiment of an air freshener according to the invention in a rotatably-coupled position with respect to the shaft.
Figure 1B:
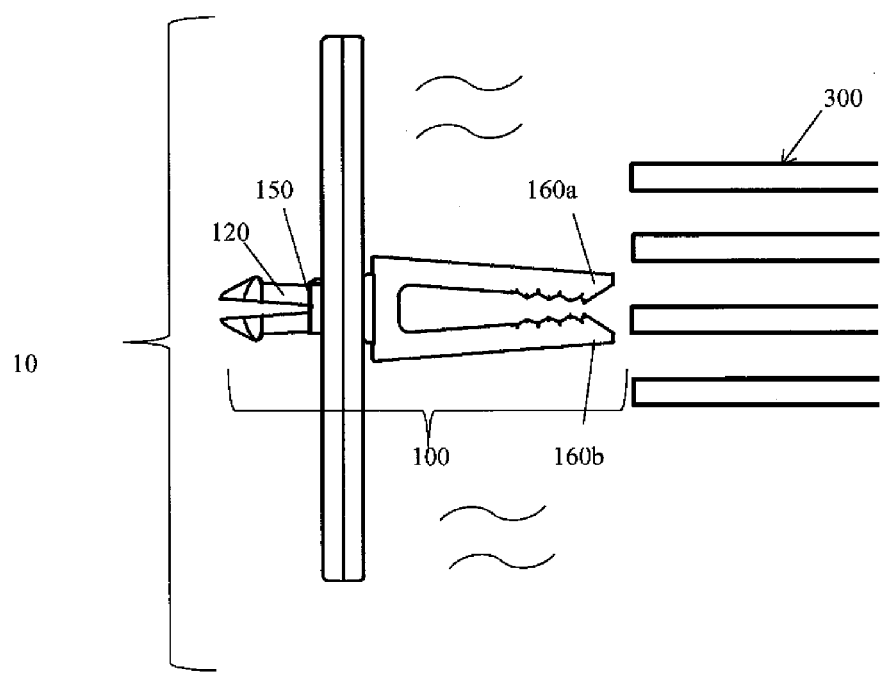
FIG. 1b is a schematic diagram that illustrates a side view of the air freshener of FIG. 1 now fixedly-coupled with respect to the shaft.

In accordance with one implementation, an embodiment is illustrated in FIG. 1 which provides an air freshener 10 constructed to mount in front of an existing air flow, such as from a vent in an automobile or residential air conditioner. The embodiment of FIG. 1 enables a user to regulate the rate that a scent is dissipated, and illustrates two positions of the disc 200. FIG. 1a show the air freshener 10 in its rotating position in which air flow from behind the air freshener causes the disc 200 to rotate and dissipate scent at a first rate. In the stationary position of FIG. 1*b*, the support 100 prevents the disc 200 from rotating even when air impinges upon the disc, and, as a consequence, scent dissipates at a second, slower rate when the disc is in this position. A user selectively places the disc 200 at one of the two positions along on the shaft 180. These dual positions allow the user to choose whether or not the disc of the air freshener is spinning and thereby control the rate at which scent dissipates. As will be appreciated from the discussion below, however, additional positions can be provided that impart different degrees of drag against rotation of the disc in order to provide additional spin rates to select.

Figure 2:
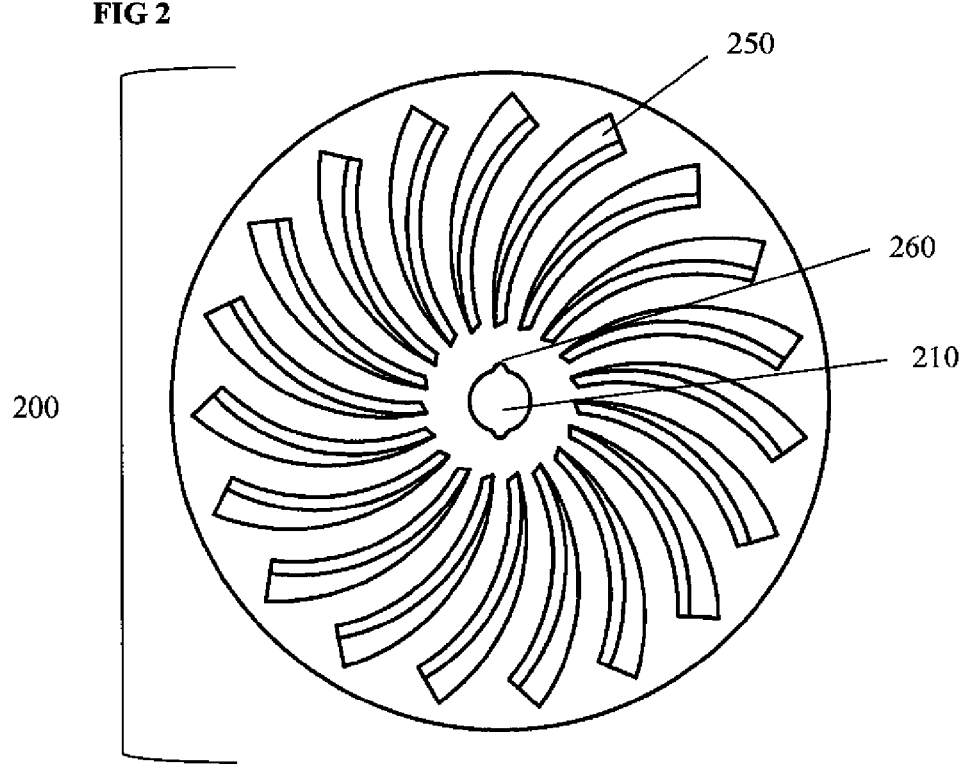
FIG. 2 illustrates a front view of the disc component of the air freshener in an example arrangement.
Figure 3:
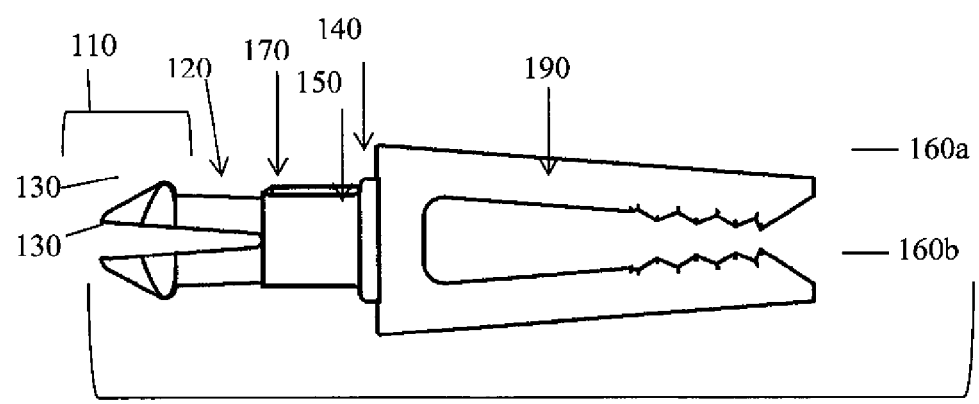
FIG. 3 shows a side view of the stem component of the air freshener in an example arrangement.

Turning now to FIG. 2, is a front view of the disc 200 illustrates its main features. The disc 200 can comprise a scented material such as a low density polyethylene or can comprise a cardboard infused with fragrance (e.g., a fragrant oil). In a preferred embodiment, the disc is made using AURACELL® brand material available from Rotuba Extruders, Inc. of Linden, N.J. For a further discussion of such a material that can be used to make the disc, see U.S. Pat. No. 7,741,266, entitled "Process for preparing scented cellulosics and products prepared thereby," issued Jun. 22, 2010, which is hereby incorporated by reference as if set forth in its entirety herein. A polyethylene disc of such constructed can be molded using conventional molding technology for scented plastics. In the illustrated embodiment, the disc may also be made from cellulose acetate or cellulose acetate ester loaded with scent.

Alternatively or in addition, the disc 200 can be manufactured using a malodor eliminating chemical compound such as described in U.S. Publication No. 20012/0167836, entitled Malodor Neutralizers In Biodegradable Substrates," which is hereby incorporated by reference as if set forth in its entirety herein. The malodor eliminator behaves the same as a fragrance when included in a plastic, i.e., it evaporates and emits from the plastic over time. What can be appreciated, therefore, is that an air freshener 10 according to any of the embodiments herein can actively eliminate offensive odors, or provide a subtle fragrance, or both, as a function of the chemical compounds included in the disc and/or the stem.

As illustrated, the embodiment of FIG. 2 has a set of airfoil surfaces 250 extending through the disc 200. The airfoils can be curved or angled or both in order to provide a surface that engages an air flow (such as from the vent 300 shown in FIG. 1A).

In the embodiment of FIG. 2, the disc has a circular shape. In other embodiments, the disc could assume a different shape. For instance, the disc could be shaped like a ventilation fan, a turbine vane, a paddle wheel, etc. In this manner, the disc 200 can be made up of blades, openings in the disc, or can be otherwise provided with apertures that are shaped to catch the air flow and impart rotation about the shaft of the support 100. The blades can be oriented at a variety of non-normal angles to the broad disc surface shown in FIG. 2 to improve rotation. Further, the face of the disc can be adorned with logos, patterns, characters, messages, or the like. As one non-limiting example, the face can be imprinted for use as a promotional item.

Returning now to FIGS. 1A and 1B, the disc 200 is removably attachable to the support 100 and has its aperture 210 locatable at one of two positions on the shaft 180. The first position 120 is sized so as to minimally resist rotation of the disc 200.

The first position 120 is defined between a head 110 at a free end of the shaft 180 and a chamfer 170. As can be seen in FIG. 3, the head includes two resiliently compressible prongs 130A, 130B (more generally, 130). The head 110 is sized to have a resting condition which is wider than the aperture 210 of the disc 200 and a stiffness that generally prevents removal of the disc except at the hand of a user. As such, the head prevents the disc from spinning off of the shaft during normal use. The prongs 130 compress to allow the head 110 to fit through the aperture 210, however, in response to action by the user in placing or removing the disc. On the other hand, the first position 120 is configured to have a dimension (e.g., diameter) which is smaller than that of the aperture 210 which enables the disc to rotate generally freely. In alternative embodiments, the aperture 210 can be fit with or seat within a ring or bearing for rotation when in the position 120.

The second position 150 is configured to prevent the disc 200 from rotating even when positioned within an air stream. In the illustrated embodiment, position 150 has a key structure or other protuberance 140 which matches indentations or key slots 260 defined along the wall of the aperture 210. The key slots 260 can rest within the key structure/protuberance 140, while a base 190 at a far end of the shaft seats the disc from further axial movement. In a preferred embodiment, the key structure/protuberance 140 is arranged along the shaft so as to be spaced away from the chamfer 170. With that arrangement, interference between the rotating disc and the key structure/protuberance 140 can be avoided even if the disc is not rotating in a vertical plane. In an alternative embodiment, position 150 can be defined by a region of the shaft 180 which has a larger dimension than the aperture of the disc, in order to frictionally engage the disc and prevent the disc from rotating. That region can extend from the chamfer 170 to the base 190.

The air freshener 10 can be attached to a car vent 300 or other source of air flow, though the vent structure forms no part of the present invention. In the illustrated embodiment, the support 100 terminates in a resilient clip 160. The clip has a base 190 and fingers 160A, 160B (more generally, 160). The fingers 160 are naturally biased towards one another but are resilient so as to receive and engage a louver the vent. In FIGS. 1A and 1B, the louver 310 is shown in a horizontal orientation. As a louver 310 is wedged between the fingers 160, the fingers separate and grip the louver. The tension of the displaced fingers holds the support and air freshener in place on the louver. Thus the air freshener 10 can be removably attached to the vent 300, and when so attached, the disc 200 is generally vertically oriented which reduces friction as it spins about the portion 120 of the shaft with minimal interference from the chamfer 170. On the other hand, if the louver 310 were vertically oriented, the fingers 160 can engage the louver and permit a generally vertical orientation for the disc 200 by rotating the clip ninety degrees and then urging the louver between the fingers. As such, a level axis can be provided for a vertically oriented plane of rotation of the disc 200 for a variety of louver orientations. In another embodiment, the air freshener can be attached to a fan of the type that has its own motor connected to a source of power in order to create an air stream. In that type of embodiment, the fan includes, among other things, a driven shaft, an impeller with a hub seated on the shaft, and fan blades coupled to the hub. A construction substantially as described can have the shaft 180 extends from the hub in a manner analogous to extending from the base 190. This positions the disc 200 in the air stream of the fan.

Embodiments of air fresheners 10 can be constructed so as to be supported in the flow of an air stream by having a single finger 160 shaped or bendable to provide a mounting surface that can mount the base as such, or with adhesive, hook and loop fasteners, suction cups, and so on.

Figure 4:
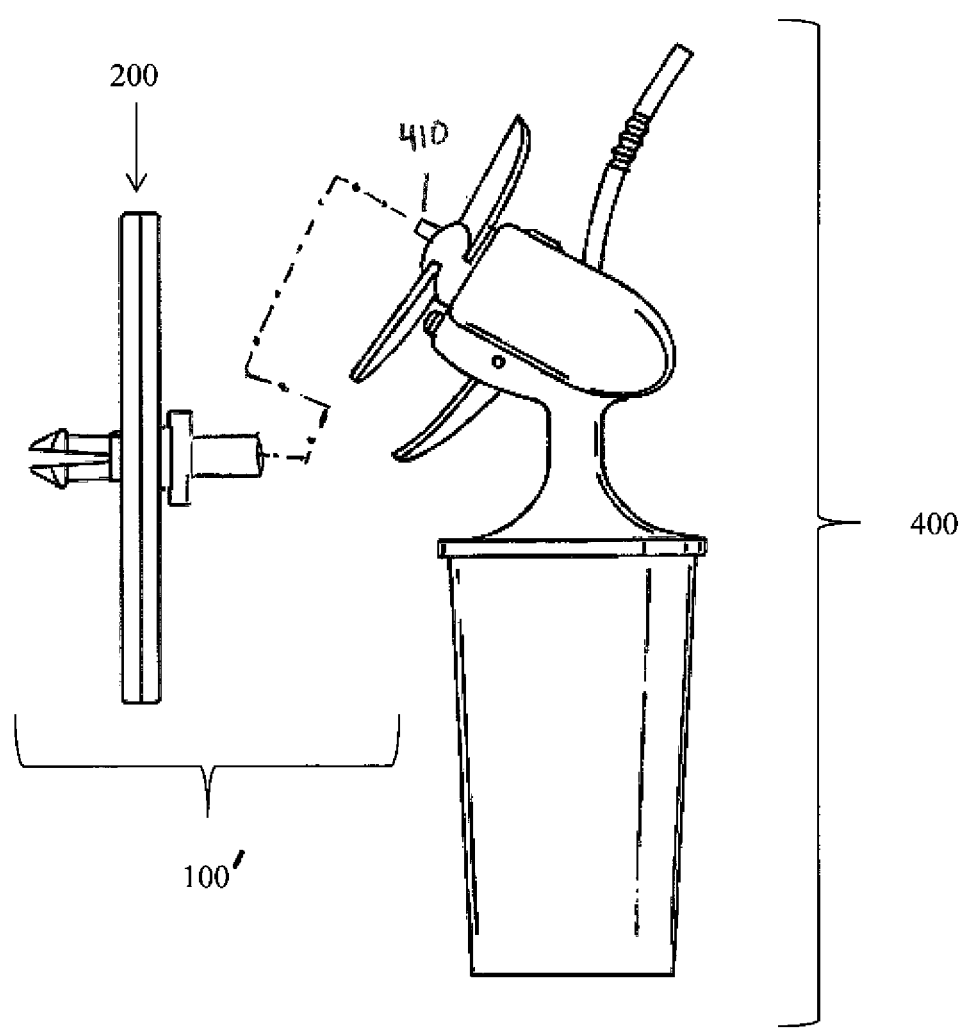
FIG. 4 shows the air freshener 10 in another example arrangement in which it combined with a novelty item.

In still further embodiments, the air freshener 10 can be combined to a fan that is attached to a novelty or toy. For instance, as in FIG. 4, a fan coupled to a bottle 400 with a nozzle with a pump arranged to provide a mist into an air stream can be combined with the stem structure 100' to support a multi-position, selectively spinnable scented disc substantially as described hereinabove. The stem can mate with the fan via a mount 410, such as by glue or a friction fit. For a discussion of one exemplary construction of a misting bottle that is suitable for use with the stem structure 100', see U.S. Pat. No. 7,143,958 B1 entitled "Misting bottle system," issued Dec. 5, 2006, which is hereby incorporated by reference as if set forth in its entirety herein. This arrangement provides a user with a scented mist. It also enables the user to personalize the fragrance or regulate the dissipation of the scent. Further, it enables the user to control the rotation of the disc. For example, a user can dissipate the scent less quickly to conserve the fragrance and selectively cause the disc 200 to remain fixed within the air stream. The disc can be in a fixed or rotatable position along the stem 100' independent of whether the fan is rotating or the pump is used to deliver a mist from the bottle.

It should be appreciated that the support 100 can also be made of a scented material, such as a scented plastic or cardboard of the types noted above. This allows users to combine fragrances and personalize the air freshener. It should also be noted that as the user can choose to rotate the disc 200 or not, in this embodiment the user will be able to control the amount of the scent from the disc 200 in the mixture. Various combinations of materials, colors, and textures can also be used to enhance aesthetic appeals and entertainment value of the air freshener. Different materials could be used for the disc, support, and clips.

In another embodiment, the described device is one part of a method for imparting a scent into an air stream. Initially a support for attachment to a vent or similar structure through which air flows is provided. For example, the support can be attached to a fan-grill or heating unit. The support has a shaft extending from a clip on one end to a free end which defines an axis of rotation. Like in other embodiments described herein, the clip can be replaced with other mechanisms for attachment, such as suction cups, adhesive, or hook-and-loop fasteners. The shaft also has a resiliently compressible head at the free end and two position options along the axis of rotation. In the present embodiment, the first position is located in front of the second to allow the disc to be repositioned quickly and easily. Next, a scented disc with a central aperture through a broad face is provided. The disc is seatable behind the head so that the head retains the disc on the support when the disc is placed behind it. The disc is then placed in one of the two positions. This step may be completed during manufacture or by the user. Further, embodiments consistent with the foregoing can enable personalized discs to be provided so that a consumer can mix and match discs and supports. In this embodiment, the consumer completes the step which attaches the support to the disc. Alternatively, a manufacturer can package theme air fresheners, such as a scent associated with a popular product or printed with images associated with a popular sports team or cartoon character. In that alternative embodiment, the manufacturer completes the step attaching the disc to the support. It should also be noted, as above, that the disc can take many forms and mechanism for imparting scents, including a scented plastic or scent-infused cardboard. The disc rotates relative to the support (e.g., shaft) while the disc is positioned along the first position of the shaft behind the head. The disc is selectively precluded from rotating relative to the stem while the disc is positioned along the second portion of the shaft. A user or manufacturer places the disc along the shaft according to preference regarding whether or not the disc is to rotate. This step can be used to regulate the dissipation of the air freshener's scent.

The described embodiments concern placement in a car. It should be noted however that the present device is easily adaptable to other settings and uses. Some of these settings have been expressly noted, as non-limiting examples. For example, the air freshener could readily be attached to the vent of a forced air heating system. It could also be easily modified to be incorporated into a toy or novelty. Other arrangements or embodiments not precisely set forth could be exercised under the teachings of the device set forth in the following claims.

Optional embodiments of the invention can be understood as including the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention have been described, it should be understood that various changes, substitutions, and alterations can be made by one of ordinary skill in the art without departing from the scope of the present invention, which is defined by the elements recited in the claims below and equivalents of such elements.

What is claimed:

1. An apparatus for imparting a scent to an air stream or for eliminating malodors, or both, comprising:
   a support in the air stream, the support having a shaft extending to a free end, and providing an axis of rotation, the shaft having first and second portions along the axis of rotation;
   a resiliently compressible head at the free end of the shaft;
   a disc having a central aperture through a face thereof which is sized to cause the head to compress while being urged thereover and being retained on the shaft when positioned therebehind, the disc being selectively positionable along the first portion of the shaft or along the second portion of the shaft and including the scent; and
   a plurality of air deflectors supported by the disc,
   wherein the aperture couples the disc for rotation when positioned by the user along the first portion of the shaft, and
   wherein the aperture fixedly couples the disc to the second portion of the shaft when positioned by the user along the second portion of the shaft.

2. The apparatus of claim 1, wherein air deflectors comprise a plurality of blades that act on the air stream.

3. The apparatus of claim 2, wherein the blades are spaced by an arrangement of openings through the disc.

4. The apparatus of claim 3, wherein the blades are oriented non-normal to the face of the disc.

5. The apparatus of claim 1, wherein the shaft includes a chamfer at a union of the first and second portions of the shaft.

6. The apparatus of claim 5, wherein the chamfer seats the disc along the first portion of the shaft.

7. The apparatus of claim 1, wherein the second portion of the shaft includes at least one protuberance, wherein the protuberance engages the aperture to preclude free rotation of the disc.

8. The apparatus of claim 1, wherein the shaft includes at least one protuberance and wherein the aperture further comprises at least one key slot, wherein the at least one protuberance is receivable in the key slot to preclude free rotation of the disc.

9. The apparatus of claim 1, wherein the disc comprises a cellulose acetate or cellulose acetate ester that is loaded with a fragrance, wherein the fragrance comprises the scent.

10. The apparatus of claim 1, further comprising a clip having a base and fingers biased toward one another, wherein the shaft is supported by the clip.

11. The apparatus of claim 10, wherein the shaft is supported by the base of the clip.

12. The apparatus of claim 1, further comprising:
a fan assembly including: a motor connected to a source of power and having a driven shaft, and an impeller comprising a hub seated on the driven shaft and fan blades coupled to the hub, wherein the fan blades provide the air stream,
wherein the shaft extends from the hub and wherein the disc is positioned in the air stream.

13. The apparatus of claim 12, further comprising:
a bottle;
a nozzle; and
a pump arranged to pump a liquid from the bottle to the nozzle and provide a mist in the air stream provided by the fan blades.

14. A method for imparting a scent to an air stream or for eliminating malodors, or both, comprising:
providing a support configured for attachment to a vent through which the air stream flows, the support having a shaft extending from a clip to a free end which defines an axis of rotation, the shaft having a resiliently compressible head at the free end and first and second portions along the axis of rotation;
providing a disc having a central aperture through a face thereof which is seatable behind the head, the head retaining the disc on the shaft when positioned therebehind, the disc including the scent;
rotating the disc relative to the shaft while the disc is positioned by the user along the first portion of the shaft behind the head; and
selectively precluding rotation of the disc relative to the shaft while the disc is positioned by the user along the second portion of the shaft.

15. The apparatus of claim 1, wherein the disc comprises a scent-infused cardboard.

16. The apparatus of claim 12, wherein the disc comprises a scent-infused cardboard.

17. The apparatus of claim 12, wherein the disc comprises a cellulose acetate or cellulose acetate ester that is loaded with a fragrance, wherein the fragrance comprises the scent.

18. The apparatus of claim 13, wherein the disc comprises a scent-infused cardboard.

19. The apparatus of claim 13, wherein the disc comprises a cellulose acetate or cellulose acetate ester that is loaded with a fragrance, wherein the fragrance comprises the scent.

* * * * *